(12) United States Patent
Nakatate et al.

(10) Patent No.: US 6,549,333 B1
(45) Date of Patent: Apr. 15, 2003

(54) ENDOSCOPE OCULAR WITH MICROSCOPE GRIPPING MECHANISM AND ENDOSCOPE HOLDER AND ENDOSCOPE FIXING METHOD

(75) Inventors: Ken-ichi Nakatate, Sakura (JP); Takashi Tsumanuma, Sakura (JP); Michiro Fuji, Tokyo (JP)

(73) Assignees: Fujikura Ltd., Tokyo (JP); M&M Co., LTD, Tokyo (JP)

(*) Notice: Subject to any disclaimer, the term of this patent is extended or adjusted under 35 U.S.C. 154(b) by 0 days.

(21) Appl. No.: 09/720,888

(22) PCT Filed: May 24, 2000

(86) PCT No.: PCT/JP00/03304
§ 371 (c)(1),
(2), (4) Date: Jan. 2, 2001

(87) PCT Pub. No.: WO00/71046
PCT Pub. Date: Nov. 30, 2000

(30) Foreign Application Priority Data

May 24, 1999 (JP) ............................................. 11-144119

(51) Int. Cl.[7] ............................................. G02B 21/00
(52) U.S. Cl. ....................... 359/368; 359/369; 359/370; 359/373
(58) Field of Search ................................. 359/368, 369, 359/370, 373, 376; 128/4, 6; 606/4; 351/205, 216

(56) References Cited

U.S. PATENT DOCUMENTS

| | | | |
|---|---|---|---|
| 3,566,872 A | * 3/1971 | Draeger et al. | 128/897 |
| 5,095,887 A | * 3/1992 | Leon et al. | 359/375 |
| 5,790,307 A | * 8/1998 | Mick et al. | 248/123.11 |
| 6,212,425 B1 | * 4/2001 | Irion et al. | 600/476 |
| 6,309,348 B1 | * 10/2001 | Schmidt et al. | 359/391 |

FOREIGN PATENT DOCUMENTS

| | | |
|---|---|---|
| JP | 6-196 | 1/1994 |
| JP | 8-131455 | 5/1996 |
| JP | 8 131456 | 5/1996 |
| JP | 8-191842 | 7/1996 |
| JP | 9-80316 | 3/1997 |

* cited by examiner

*Primary Examiner*—Mohammad Sikder
(74) *Attorney, Agent, or Firm*—Chadbourne & Parke, LLP

(57) ABSTRACT

An endoscope ocular portion fitted with a microscope gripping mechanism 9 is adopted where a microscope gripping mechanism 10 has; a microscope gripping portion 12 for gripping a microscope ocular portion 11a of a medical microscope 11, an endoscope securing portion 14 secured to an endoscope ocular portion 13a, and a linkage portion 16 linking the microscope gripping portion 12 and endoscope securing portion 14, and positioning and securing the endoscope ocular portion 13a and the microscope ocular portion 11a on the same virtual plane 15 and at approximately the same spacing W as the pupil distance of an observer. According to this endoscope ocular portion fitted with a microscope gripping mechanism 9, observation of both the medical microscope and the endoscope at the same time without the observer significantly moving their head or body, is possible at low cost.

14 Claims, 15 Drawing Sheets

FIG. 19
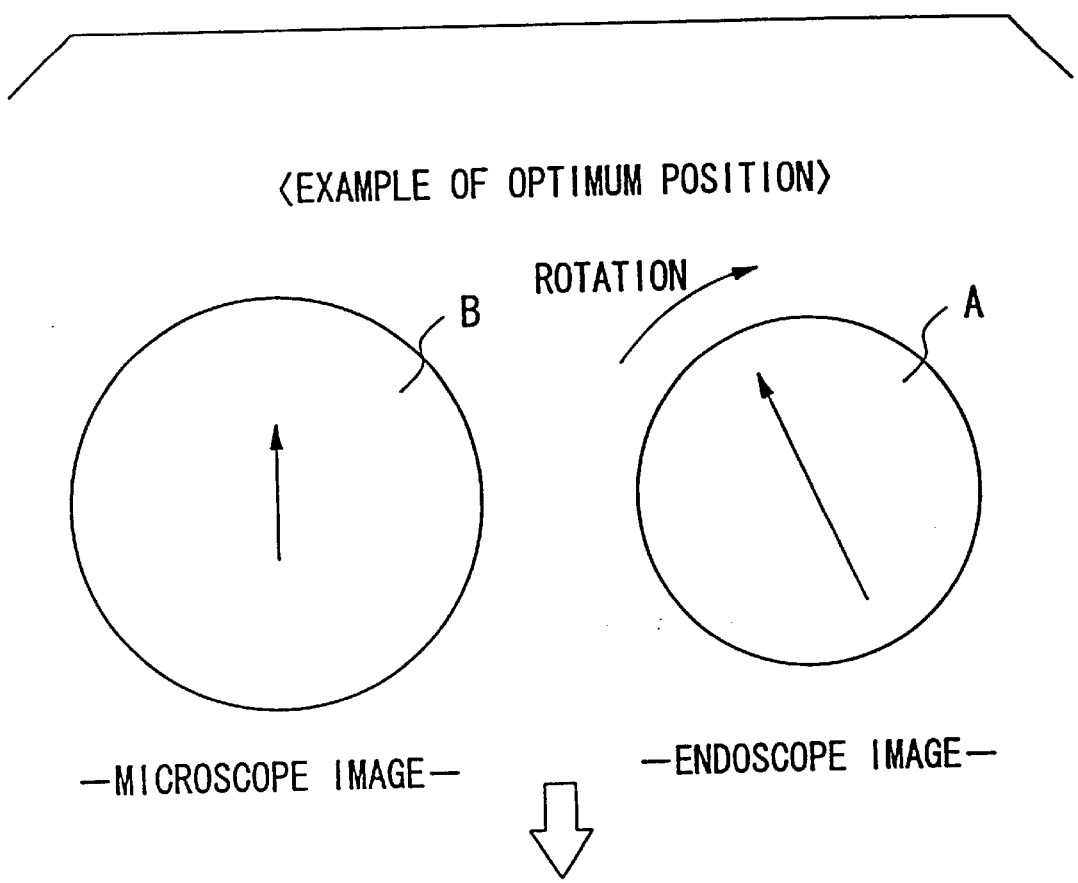
⟨EXAMPLE OF OPTIMUM POSITION⟩
—MICROSCOPE IMAGE—  —ENDOSCOPE IMAGE—
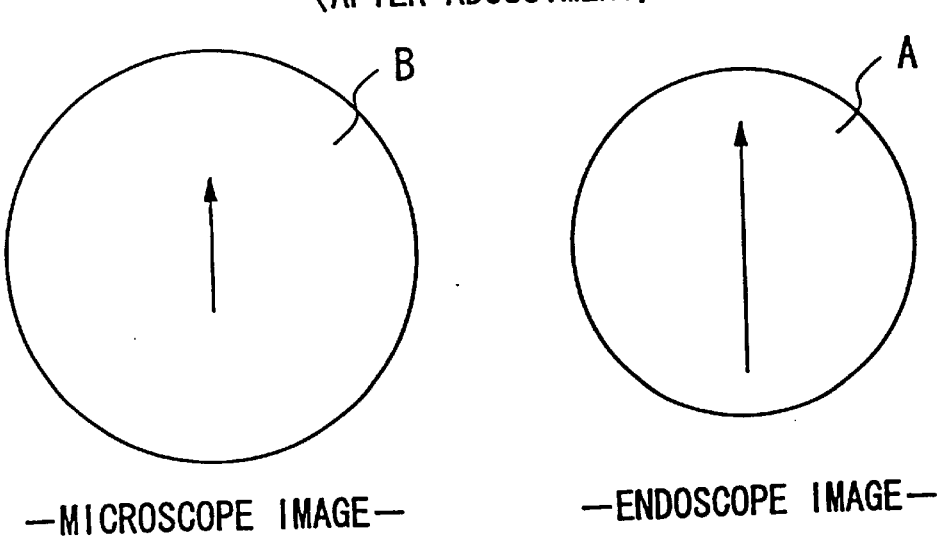
⟨AFTER ADJUSTMENT⟩
—MICROSCOPE IMAGE—  —ENDOSCOPE IMAGE—

ENDOSCOPE OCULAR WITH MICROSCOPE GRIPPING MECHANISM AND ENDOSCOPE HOLDER AND ENDOSCOPE FIXING METHOD

TECHNICAL FIELD

The present invention relates to an endoscope ocular portion fitted with a microscope gripping mechanism and an endoscope holder and endoscope securing method, whereby an endoscope or an endoscope ocular portion can be secured to a medical microscope.

BACKGROUND ART

Many operations such as neurosurgery or ophthalmology are carried out under a microscope. However heretofore, in the case where an endoscope is used under such circumstances, in order to view the endoscope image, as shown in FIG. 27, the eye is separated from the microscope ocular portion 1a of the medical microscope to look into the endoscope ocular portion 2a of the endoscope (the bottom left figure), or to view the endoscope image received by an imaging device 3 which is branch connected to the endoscope 2, with a monitor 4 (bottom right figure).

However, this has the following problems. That is to say, in order to view the endoscope image, the observer must move significantly, for example raising the face and changing the position of the body, which is inconvenient. Furthermore, since both the microscope image of the medical microscope 1 and the endoscope image of the endoscope 2 cannot be observed at the same time, this also has the problem in that it is difficult to determine the position for performing observation with the endoscope 2, making operation difficult.

As a particular example, there is also a system for displaying the endoscope image overlapped within the microscope field of vision using an optical/electrical device (not shown in the figure). However the apparatus for this is expensive, and is not one which can be applied to any microscope.

The present invention takes into consideration the above situation, with the object of providing an endoscope ocular portion fitted with a microscope gripping mechanism and an endoscope holder and an endoscope securing method, whereby simultaneous viewing of a medical microscope and an endoscope without the observer significantly moving their face or head, can be realized at low cost.

DISCLOSURE OF THE INVENTION

The endoscope ocular portion fitted with a microscope gripping mechanism is one where a microscope gripping mechanism for gripping a medical microscope is provided on the endoscope ocular portion, and is characterized in that the microscope gripping mechanism has; a microscope gripping portion for gripping the medical microscope, an endoscope securing portion secured to the endoscope ocular portion, and a linkage portion linking the microscope gripping portion and endoscope securing portion, and positioning and securing the endoscope ocular portion and a microscope ocular portion of the medical microscope on the same virtual plane and at approximately the same spacing as the pupil distance of an observer.

According to this endoscope ocular portion fitted with a microscope gripping mechanism, the endoscope ocular portion fitted with the microscope gripping mechanism is attached to the medical microscope so that the endoscope ocular portion and the microscope ocular portion are on the same virtual plane, and are at approximately the same spacing as the pupil distance of the observer. Hence the observer can view both the microscope image and the endoscope image while looking at the microscope ocular portion with one eye, and at the same time looking at the endoscope ocular portion with the other eye. Consequently, with such an endoscope ocular portion fitted with a microscope gripping mechanism, the microscope image of the medical microscope and the endoscope image of the endoscope can be observed at the same time without the observer significantly moving their head or body. Moreover, since this involves a low cost construction, then this can be realized at a low cost.

Furthermore, the endoscope ocular portion fitted with a microscope gripping mechanism of the present invention is characterized in that with the endoscope securing portion, the relative position in the horizontal direction, the vertical direction and the rotation direction is adjustable with respect to the microscope gripping portion, and the inclination is adjustable with respect to the axis of the microscope gripping portion.

With such an endoscope ocular portion fitted with a microscope gripping mechanism, by operating the linkage portion of the microscope gripping mechanism, and adjusting the relative positions in the horizontal, the vertical and the rotation direction of the endoscope securing portion with respect to the microscope gripping portion, and adjusting the inclination of the axis of the endoscope securing portion with respect to the axis of the microscope gripping portion, the endoscope ocular portion can be positioned and secured at an optimum position for easy observation corresponding to the direction and position of the body or head of the observer.

Furthermore, the endoscope ocular portion fitted with a microscope gripping mechanism of the present invention, is characterized in that there is provided an optical-electrical device whereby with the endoscope ocular portion, an endoscope image can be directly view with the naked eye, and at the same time the endoscope image can be separately displayed and recorded.

With the endoscope ocular portion fitted with a microscope gripping mechanism, the endoscope image is viewed directly with the naked eye, and at the same time recording and display is affected by means of the optical-electrical device. By means of this display, the endoscope image can be viewed by several observers at the same time with the naked eye.

Moreover, with the endoscope ocular portion fitted with a microscope gripping mechanism of the present invention, the linkage portion links so that a plurality of separate arms can be folded and unfolded therebetween, and one end separate arm is connected to the endoscope securing portion, and an other end separate arm is connected to the microscope gripping portion so as to be slidably moveable in the axial direction of the microscope ocular portion.

According to the endoscope ocular portion fitted with a microscope gripping mechanism, by folding or unfolding while widening or narrowing the angle of the respective separate arm spacing, the spacing dimension between the microscope ocular portion and the endoscope ocular portion can be easily adjusted to conform to the pupil distance dimension of the observer. Furthermore, by slidingly moving the endoscope securing portion together with the endoscope in the axial direction being the site line direction at the time of looking into the microscope attached to these, with respect to the microscope gripping portion, the endoscope ocular portion and the microscope ocular portion can be easily adjusted to approximately the same height.

Furthermore, the endoscope holder of the present invention is an endoscope holder which secures and holds an endoscope such as a fiberscope or an endoscope ocular portion to a medical microscope, and is characterized in having; a microscope securing portion secured to the medical microscope, an endoscope holding portion for holding the endoscope or the endoscope ocular portion, and a linkage portion linking the microscope securing portion and endoscope holding portion, and positioning and securing the endoscope ocular portion or the endoscope ocular portion of the endoscope and a microscope ocular portion of the medical microscope on the same virtual plane and at approximately the same spacing as the pupil distance of an observer.

According to this endoscope holder, the microscope securing portion is attached and secured to the medical microscope and the endoscope or the endoscope ocular portion is held on the endoscope holding portion, so that the endoscope ocular portion and the microscope ocular portion are on the same virtual plane, and are at approximately the same spacing as the pupil distance of the observer. Hence the observer can view both the microscope image and the endoscope image while looking at the microscope ocular portion with one eye, and at the same time looking at the endoscope ocular portion with the other eye. Consequently, with such an endoscope holder, the microscope image of the medical microscope and the endoscope image of the endoscope can be observed at the same time without the observer significantly moving their head or body. Moreover, since this involves a low cost construction, then this can be realized at a low cost.

Moreover, with the endoscope holder of the present invention, the endoscope holding portion can adjust the relative position in the horizontal direction, the vertical direction and the rotation direction with respect to said microscope securing portion, and can adjust the inclination with respect to the axis of the microscope securing portion.

With such an endoscope holder, by operating the linkage portion and adjusting the relative positions in the horizontal direction, the vertical direction and the rotation direction of the endoscope holding portion with respect to the microscope securing portion, and adjusting the inclination of the axis of the endoscope securing portion with respect to the axis of the microscope securing portion, the endoscope ocular portion or the endoscope can be positioned and secured at an optimum position for easy observation corresponding to the direction and position of the body or head of the observer.

Furthermore, with the endoscope holder of the present invention, the linkage portion links so that a plurality of separate arms can be folded and unfolded therebetween, and one end separate arm is connected to the endoscope holding portion, and an other end separate arm is connected to the microscope securing portion so as to be slidably moveable in the axial direction of the microscope ocular portion.

According to the endoscope holder, by folding or unfolding while widening or narrowing the angle of the respective separate arm spacing, the spacing dimension between the microscope ocular portion and the endoscope ocular portion can be adjusted to conform to the pupil distance dimension of the observer. Furthermore, by slidingly moving the endoscope holding portion together with the endoscope in the axial direction being the site line direction at the time of looking into the microscope attached to these, with respect to the microscope securing portion, the endoscope ocular portion and the microscope ocular portion can be adjusted to approximately the same height.

Furthermore, an endoscope securing method according to the present invention is one where an endoscope such as a fiberscope or an endoscope ocular portion is secured to a medical microscope, and involves securing via a linkage portion an endoscope holding portion which holds the endoscope or the endoscope ocular portion, to a microscope securing portion which is secured to the medical microscope, and positioning and securing the endoscope ocular portion of the endoscope or the endoscope ocular portion and a microscope ocular portion of the medical microscope on the same virtual plane and at approximately the same spacing as the pupil distance of an observer.

According to this endoscope securing method, by positioning and securing the endoscope ocular portion and the microscope ocular portion on the same virtual plane and at approximately the same spacing as the pupil distance of an observer, the observer can view both the microscope image and the endoscope image, looking at the microscope ocular portion with one eye, while looking at the endoscope ocular portion with the other eye.

Furthermore, with the endoscope securing method of the present invention, the linkage portion links so that a plurality of separate arms can be folded and unfolded therebetween, and one end separate arm is connected to the endoscope holding portion, and an other end separate arm is connected to the microscope securing portion so as to be slidably moveable in the axial direction of the microscope ocular portion.

According to the endoscope securing method, by folding or unfolding while widening or narrowing the angle of the respective separate arm spacing, the spacing dimension between the microscope ocular portion and the endoscope ocular portion can be adjusted to conform to the pupil distance dimension of the observer. Furthermore, by slidingly moving the endoscope holding portion together with the endoscope in the axial direction being the site line direction at the time of looking into the microscope attached to these, with respect to the microscope securing portion, the endoscope ocular portion and the microscope ocular portion can be adjusted to approximately the same height.

Furthermore, the endoscope ocular portion fitted with a microscope gripping mechanism, or the endoscope holder, or the endoscope securing method of the present invention, is characterized in that said linkage portion enables said respective separate arms to be folded and unfolded within a vertical plane.

With the endoscope ocular portion fitted with a microscope gripping mechanism, or the endoscope holder, or the endoscope securing method, at the time of adjusting the spacing of the microscope ocular portion and the endoscope ocular portion, the separate arms of the connecting portion are folded within the vertical plane. Therefore after folding, the separate arms do not stick out in the horizontal direction. Hence the situation where it is difficult to see due to the nose etc. of the observer being bumped on the separate arms when making an observation does not arise.

BRIEF DESCRIPTION OF THE DRAWINGS

FIG. 19 is an explanatory diagram for explaining adjustment of the endoscope image direction of the endoscope which is held using the microscope gripping mechanism.

BEST MODE FOR CARRYING OUT THE INVENTION

In order to better explain the present invention, a description is now given in accordance with the accompanying drawings.

The endoscope ocular portion fitted with a microscope gripping mechanism of the present invention is one where a microscope gripping mechanism for gripping a medical microscope is provided on the endoscope ocular portion. An embodiment thereof will be described hereunder with reference to the drawings, however the present invention is not to be interpreted in any way as limited to this.

With the present invention, the basic construction is one where a microscope gripping mechanism is provided integral with an endoscope ocular portion which is separated from the endoscope body (scope portion) such as a fiberscope. However, in addition to this, a construction can also be adopted where the endoscope holding mechanism is used as a single unit as an endoscope holder for securing and holding the endoscope body or the endoscope ocular portion to a medical microscope. Accordingly, the description will be made centered on a microscope gripping mechanism (endoscope holder) being the constituent of the present invention.

Figure 1:
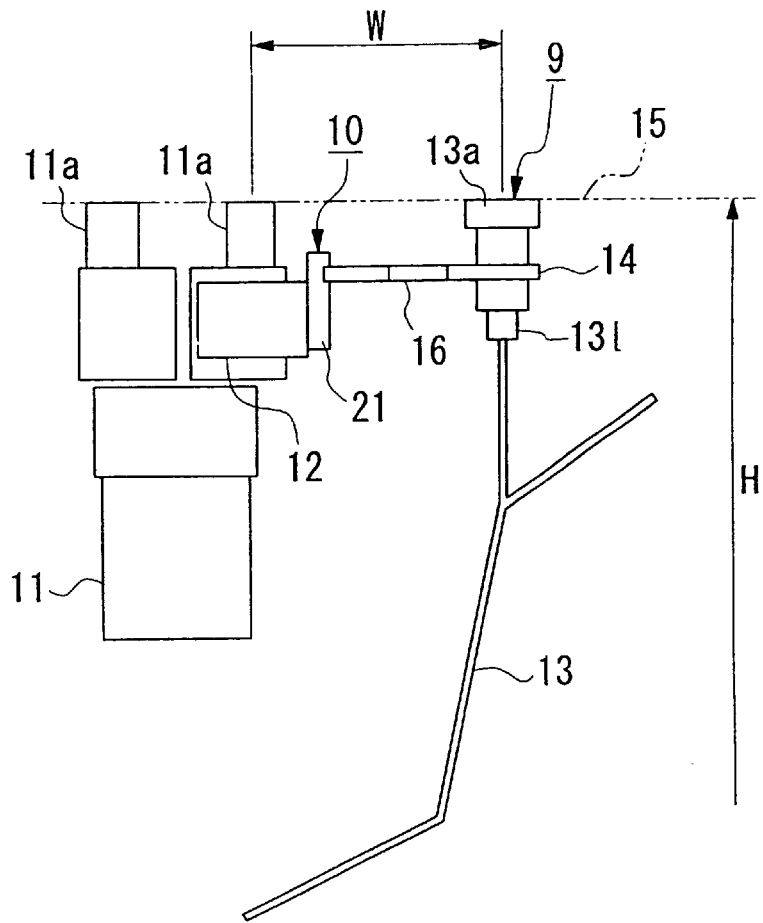
FIG. 1 is an elevation view showing a working layout of a microscope gripping mechanism of the present invention.
Figure 2:
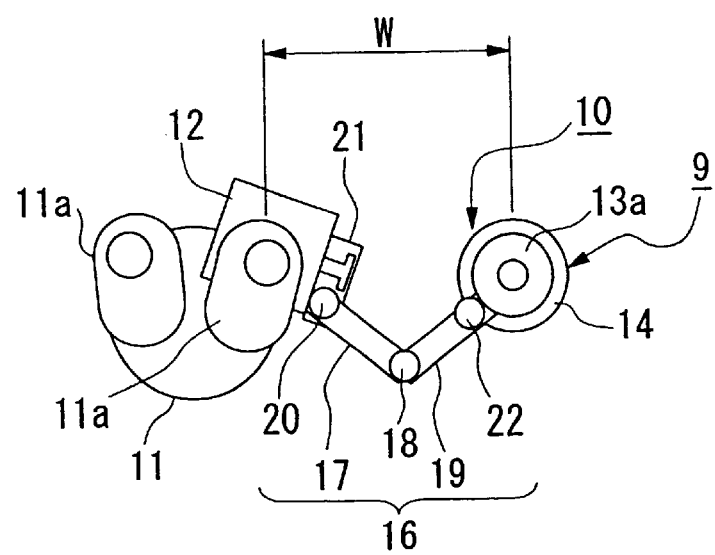
FIG. 2 is a plan view showing the microscope gripping mechanism of FIG. 1.

As shown in FIG. 1 and FIG. 2, with an endoscope ocular portion 9 fitted with a microscope gripping mechanism of this embodiment, the microscope gripping mechanism 10 (endoscope holder 10) comprises; a microscope gripping portion 12 (microscope securing portion 12) for gripping a medical microscope 11, an endoscope securing portion 14 (endoscope holding portion 14) secured to an ocular portion 13a of an endoscope 13, and a linkage portion 16 connecting between the microscope gripping portion 12 and the endoscope securing portion 14 for positioning and securing the endoscope ocular portion 13a and the microscope ocular portion 11a so as to have approximately the same height H, and be positioned on the same virtual plane 15 and at approximately the same spacing dimension W as the pupil distance dimension of an observer. Here reference symbol 13l denotes a connector.

Moreover, with the endoscope securing portion 14, the linkage portion 16 links so that a plurality of separate arms (a first separate arm 17 and a second separate arm 19) can be folded and unfolded therebetween. The second separate arm 19, being one end separate arm, is connected to the endoscope securing portion 14, and the first separate arm 17, being an other end separate arm, is connected to the microscope gripping portion 12 so as to be slidably moveable in the axial direction of the microscope ocular portion 11a. Therefore, by means of the linkage portion 16, the relative position in the horizontal direction, the vertical direction and the rotation direction is adjustable with respect to the microscope gripping portion 12, and the inclination of the axis of the endoscope securing portion 14 is adjustable with respect to the axis of the microscope gripping portion 12.

That is to say, the linkage portion 16, in the view shown in FIG. 2, has a first separate arm 17, and a second separate arm 19 connected to the first separate arm 17 by a pin 18 so as to turn thereabout, and the first separate arm 17 is connected via a slide member 21 to the microscope gripping portion 12 by a pin 20 so as to turn thereabout. Furthermore, the endoscope securing portion 14 is connected by a pin 22 to the second separate arm 19 so as to turn thereabout. Accordingly, with the pin 18, the pin 20 and the pin 22 as joints, the first separate arm 17 can turn with respect to the microscope gripping portion 12, the second separate arm 19 can turn with respect to the first separate arm 17, and the endoscope securing portion 14 can turn with respect to the second separate arm 19, about respective axes perpendicular to the page in FIG. 2. Therefore, the spacing dimension W can be adjusted to conform to the pupil distance dimension of the observer. Here, in order to produce an appropriate resistance to the turning operation in the respective pins 18, 20 and 22, an appropriate friction is provided so that these do not turn except when a force is applied.

Furthermore, the slide member 21 is engaged with a side portion of the microscope gripping portion 12 so as to be slideably movable in the axial direction of the microscope ocular portion 11a, being the direction perpendicular to the page of FIG. 2 (however in order to prevent this coming away from the microscope gripping portion 12 due to sliding movement other than when required, the sliding movement length is restricted by a stopper (not shown in the figure)). The engagement portion of the slide member 21 and the microscope gripping portion 12 is given an appropriate friction to prevent sliding except when a force is applied. In this way, the linkage portion 16 and the endoscope securing portion 14 can be raised and lowered in the height H direction in FIG. 1 so that the vertical position thereof can be adjusted to correspond to the lengthwise form of the endoscope ocular portion 13a. This enables positional adjustment to the same virtual plane 15 so that the endoscope ocular portion 13a and the microscope ocular portion 11a have approximately the same height H. Moreover, the engaging portion of the slide member 21 rotates with respect to the microscope gripping portion 12 only when a force is applied, enabling the inclination of the axis of the endoscope securing portion 14 with respect to the axis of the microscope gripping portion 12 to also be adjusted.

Here, for the linkage portion 16, provided that the endoscope securing portion 14 can be relatively positioned in the horizontal direction and the vertical direction with respect to the microscope gripping portion 12, and the inclination with respect to the axis of the microscope gripping portion 12 can be adjusted, then other constructions such as shown in FIG. 3 through FIG. 6 may be adopted.

Figure 3:
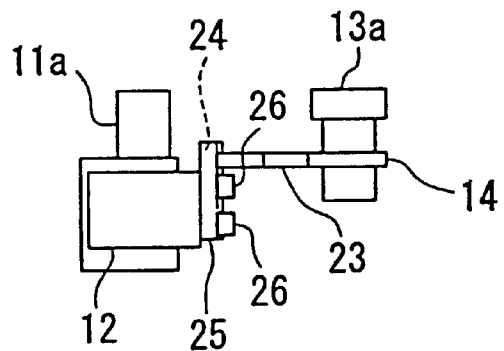
FIG. 3 is an elevation view showing a modified example of a connecting portion of the microscope gripping mechanism of FIG. 1.

That is to say, the linkage portion 23 shown in FIG. 3 (in order to differentiate from the linkage portion 16 the reference numerals are changed. With FIG. 4 through FIG. 6 also, the reference numerals are similarly changed.) comprises; a threaded rod 24 supportingly secured to a side portion of the microscope gripping portion 12 with the vertical direction as the axis, a slide member 25 in which is formed a through hole for taking the threaded rod 24, and adjusting screws 26 rotatably attached to the slide member 25 in a condition with the threaded rod 24 threadedly engaged inside the through hole. The adjusting screws 26 are given a suitable friction, so that they do not rotate except when a force is applied. With such a construction, by rotating the adjusting screw 26, these move in the axial direction of the threaded rod 24, and hence the whole of the linkage portion 23 slides in the up/down direction, being the axial direction of the threaded rod 24, so that the height of the endoscope ocular portion 13a with respect to the microscope ocular portion 11a can be adjusted (in order to prevent this from sliding and coming away from the microscope gripping portion 12 other than when required, the sliding movement length is restricted by a stopper (not shown in the figure)). Furthermore, the slide member 25 rotates with respect to the microscope gripping portion 12 only when a force is applied, enabling the inclination of the axis of the endoscope securing portion 14 with respect to the axis of the microscope gripping portion 12 to also be adjusted.

Figure 4:
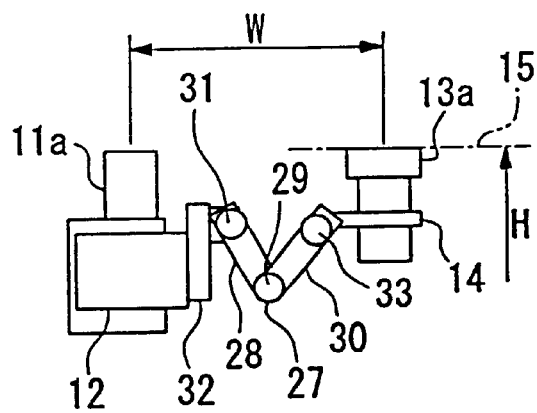
FIG. 4 is an elevation view showing another modified example of a connecting portion of the microscope gripping mechanism of FIG. 1.

Furthermore, the linkage portion 27 shown in FIG. 4, in the view of FIG. 4, has a third separate arm 28, and a fourth separate arm 30 connected to the third separate arm 28 by a pin 29 so as to turn thereabout, and the third separate arm 28 is connected via a slide member 32 to the microscope gripping portion 12 by a pin 31 so as to turn thereabout. Furthermore, the endoscope securing portion 14 is connected by a pin 33 to the fourth separate arm 30 so as to turn thereabout. Accordingly, with the pin 29, the pin 31 and the pin 33 as joints, the third separate arm 28 can turn with respect to the microscope gripping portion 12, the fourth separate arm 30 can turn with respect to the third separate arm 28, and the endoscope securing portion 14 can turn with respect to the fourth separate arm 30, about respective axes perpendicular to the page in FIG. 4. Therefore, the spacing dimension W can be adjusted to conform to the pupil distance dimension of the observer. Here, in order to produce an appropriate resistance to the turning operation in the respective pins 29, 31 and 33, an appropriate friction is provided so that these do not turn except when a force is applied.

Moreover, this slide member 32 has the same construction as the slide member 21. The linkage portion 27 and the endoscope securing portion 14 can be raised and lowered in the height H direction in FIG. 3 so that the vertical position thereof can be adjusted to correspond to the lengthwise form of the endoscope ocular portion 13a. This enables positional adjustment to the same virtual plane 15 so that the endoscope ocular portion 13a and the microscope ocular portion 11a have approximately the same height H. Moreover, the slide member 32 rotates with respect to the microscope gripping portion 12 only when a force is applied, enabling the inclination of the axis of the endoscope securing portion 14 with respect to the axis of the microscope gripping portion 12 to also be adjusted.

With the above described linkage portion 27, basically, the attachment direction of the linkage portion 16 in FIG. 2 is changed from horizontal to vertical. However since the construction is adopted where the third separate arm 28 and the fourth separate arm 30 can be folded and unfolded within the vertical plane, after folding, the third separate arm 28 or the fourth separate arm 30 do not stick out in the horizontal direction. Hence the situation where it is difficult to see due to the nose etc. of the observer being bumped when making an observation does not arise.

Figure 5:
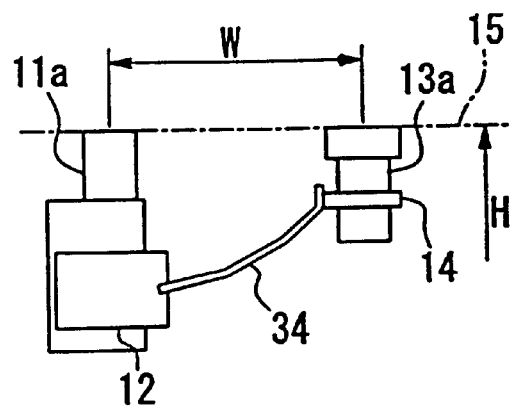
FIG. 5 is an elevation view showing another modified example of a connecting portion of the microscope gripping mechanism of FIG. 1

Furthermore, the linkage portion 34 shown in FIG. 5 is a flexible arm which can be bent at any position along the lengthwise direction, and one end thereof is fixed to the microscope gripping portion 12, and the endoscope securing portion 14 is fixed to the other end. This flexible arm is bent by applying a force, and after bending, the condition after bending can be maintained provided a force is not applied.

By using the linkage portion 34 having the construction as described above, the relative position in the horizontal direction and the vertical direction of the endoscope securing portion 14 can be adjusted with respect to the microscope gripping portion 12, and the inclination of the axis of the endoscope securing portion 14 can be adjusted with respect to the axis of the microscope gripping portion 12. Therefore, the endoscope ocular portion 13a and the microscope ocular portion 11a can be adjusted to approximately the same height H, and the spacing dimension W thereof can be adjusted to approximately the same as the pupil distance dimension of the observer.

Figure 6:
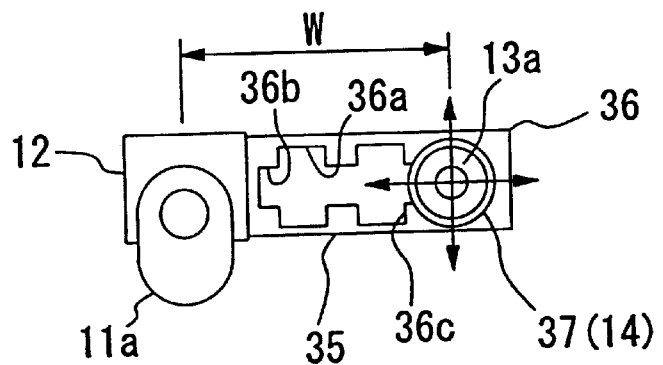
FIG. 6 is a plan view showing another modified example of a connecting portion of the microscope gripping mechanism of FIG. 1

Furthermore, a linkage portion 35 shown in FIG. 6, has a plate like guide plate 36 formed with guide groove 36a, and secured horizontally to a side portion of the microscope gripping portion 12, and an endoscope guide member 37 (the endoscope securing portion 14) attached inside the guide groove 36a so as to be moveable horizontally. The guide groove 36a comprises a transverse groove 36b formed in the lengthwise direction of the guide plate 36, and longitudinal grooves 36c severally formed perpendicular thereto. By moving the endoscope guide member 37 along the transverse groove 36b, the spacing dimension W between the endoscope ocular portion 13a and the microscope ocular portion 11a can be adjusted to approximately the same as the pupil distance dimension of the observer. Moreover, by moving the endoscope guide member 37 along the longitudinal grooves 36c, the horizontal direction position of the endoscope ocular portion 13a with respect to the microscope ocular portion 11a can be adjusted. Furthermore, the endoscope guide member 37 can also be moved in the thickness direction of the guide plate 36 inside the guide groove 36a. Therefore the height of the endoscope ocular portion 13a can also be adjusted to approximately the same height H of the microscope ocular portion 11a.

Next for a method of securing the microscope gripping portion 12 to the microscope ocular portion 11a, a description is given of a securing method shown for example in FIG. 7 through FIG. 15. Although not shown in FIG. 7 through FIG. 15, it is possible to grip portions other than the microscope ocular portion 11a.

Figure 7:
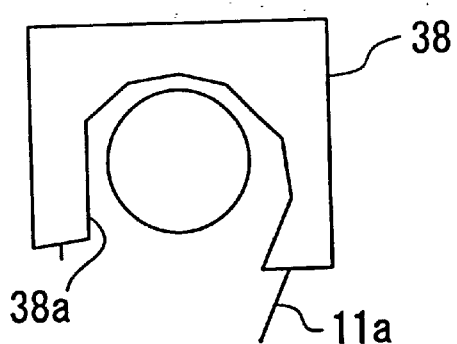
FIG. 7 is a plan view showing a microscope gripping portion of the microscope gripping mechanism of FIG. 1.

That is to say, in a microscope gripping portion 38 shown in FIG. 7 (in order to differentiate from the microscope gripping portion 12, the reference numeral is changed. With FIG. 8 through FIG. 15 also, the reference numerals are similarly changed.), is formed an engaging groove 38a of a shape which conforms to the external shape of the microscope ocular portion 11a. The microscope gripping portion 38 is fixed from above the microscope ocular portion 11a so that the microscope ocular portion 11a passes inside the engaging groove 38a. The shape of the engaging groove 38a is a shape which engages with a part of the microscope ocular portion 11a where the cross-section is other than circular shape (for example a part of the polygon shape shown in FIG. 7) such that the microscope gripping portion 38 will not turn about the microscope ocular portion 11a. Furthermore, by making the lower end face of the microscope gripping portion 38 abut with the microscope ocular portion 11a at the time of fitting, further movement of the microscope ocular portion 11a in the axial direction is restricted.

Figure 8:
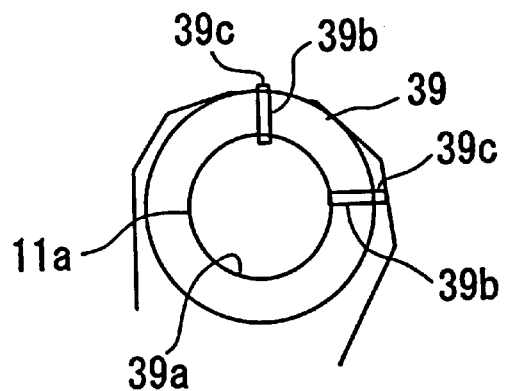
FIG. 8 is a plan view showing a modified example of a microscope gripping portion of the microscope gripping mechanism of FIG. 1.

Moreover, as a method of securing to a circular shape cross-section portion, as with the body tube portion of the microscope ocular portion 11a shown in FIG. 8, there is a method which uses a microscope gripping portion 39 shown in the same figure. With this microscope gripping portion 39, an engaging hole 39a of a shape which conforms to the external shape of the body tube portion is formed. The microscope ocular portion 11a passes inside the engaging hole 39a, and a male screw 39c threadedly engaged inside a female screw hole 39b formed in a direction perpendicular to the axis of the body tube portion is tightened, so as to press against and secure the side face of the body tube portion. By means of such a construction, the microscope gripping portion 39 clamps the body tube portion of the microscope ocular portion 11a between the engaging hole 39a and the male screw 39c. Hence the microscope ocular portion 11a is secured so as not to rotate and not to move in the axial direction of the body tube portion.

Figure 9:
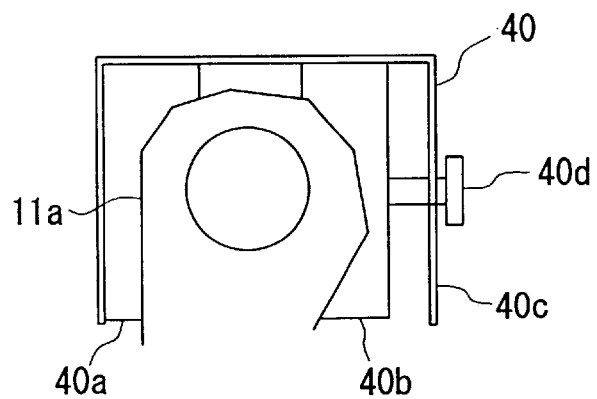
FIG. 9 is a plan view showing another modified example of a microscope gripping portion of the microscope gripping mechanism of FIG. 1.

Furthermore, as a similar screw securing method, there is also a method which uses a microscope gripping portion 40 shown in FIG. 9. This microscope gripping portion 40 is constructed with; a pair of clamp members 40a, 40b for clamping the microscope ocular portion 11a from the side, a holding member 40c of C-shape in cross-section for accommodating and holding these, and a male screw 40d threadedly engaged in a female screw hole formed in the sideways direction of the holding member 40c so as to be perpendicular to the axis of the microscope ocular portion 11a for pushing the clamp member 40b towards the clamp member 40a. The faces of the clamp member 40a and the clamp member 40b which abut against the microscope ocular portion 11a are each formed in a shape to conform to the external shape of the microscope ocular portion 11a. By tightening the male screw 40d, the microscope gripping portion 40 can be secured so as not to rotate about the axis of the microscope ocular portion 11a and so as not to move in the axial direction. The clamp member 40a is secured by bonding or the like to inside the holding member 40c.

Figure 10:
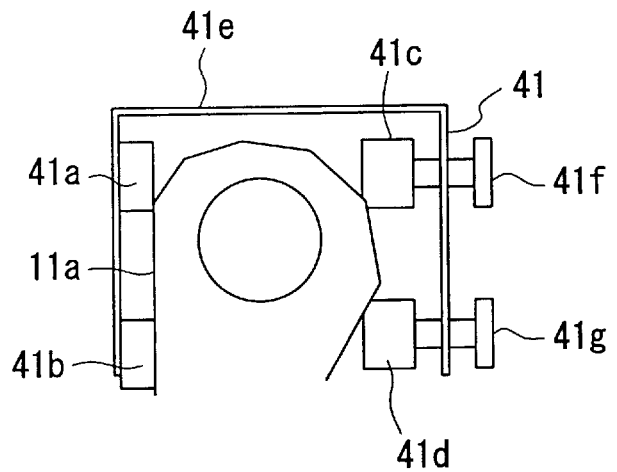
FIG. 10 is a plan view showing another modified example of a microscope gripping portion of the microscope gripping mechanism of FIG. 1.

As a similar screw securing method, there is also a method which uses a microscope gripping portion 41 shown in FIG. 10. With this method, instead of the above mentioned clamp members 40a and 40b of FIG. 9, the microscope ocular portion 11a is clamped at four points inside a holding member 40e of C-shape in cross-section by means of resilient bodies 41a, 41b, 41c and 41d made of rubber or the like. The resilient bodies 41a and 41b are secured to the inner face of the holding member 40e by bonding or the like, while the resilient bodies 41c and 41d are respectively attached to the ends of two male screws 41f and 41g. The male screws 41f and 41g are respectively threaded inside female screw holes formed at two locations in the holding member 41e, and by tightening these, the resilient bodies 41c and 41d are pushed towards the resilient bodies 41a and 41b, thereby enabling the microscope gripping portion 41 to be secured so as not to rotate about the axis of the microscope ocular portion 11a and so as not to move in the axial direction.

Figure 11:
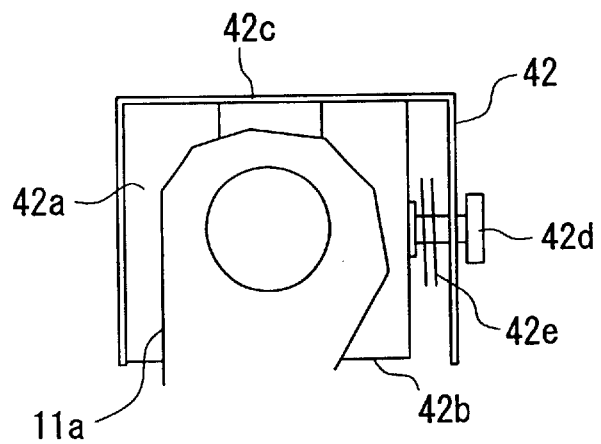
FIG. 11 is a plan view showing another modified example of a microscope gripping portion of the microscope gripping mechanism of FIG. 1.

Furthermore, as shown in FIG. 11, there is also a securing method where securing to the microscope ocular portion 11a is affected using a spring. That is to say, a microscope gripping portion 42 of FIG. 11 is constructed with; a pair of clamp members 42a, 42b for clamping the microscope ocular portion 11a from both sides, a holding member 42c of C-shape in cross-section for accommodating and holding these, a push rod 42d slideably inserted into a through hole formed in the side of the holding member 42c at right angles to the axis of the microscope ocular portion 11a, and a spring 42e coaxial with the push rod 42d, and urging towards the clamp member 42b. The clamp member 42a is secured to the inner face of the holding member 42c by bonding or the like. Accordingly, by pulling the push rod 42d so as to compress the spring 42e, the space between the clamp member 42a and the clamp member 42b is widened, after which the microscope ocular portion 11a is passed therethrough. Then by releasing the push rod 42d, the clamp member 42b is urged towards the microscope ocular portion 11a by the spring 42e. Therefore the microscope ocular portion 11a is clamped and secured between the clamping members 42a and 42b.

Figure 12:
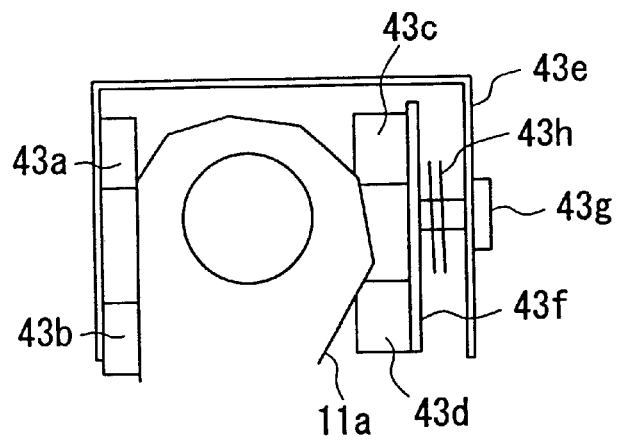
FIG. 12 is a plan view showing another modified example of a microscope gripping portion of the microscope gripping mechanism of FIG. 1.

Furthermore, as a securing method similarly using a spring, there is a securing method shown in FIG. 12. That is to say, a microscope gripping portion 43 is one where, instead of the abovementioned clamping members 42a and 42b of FIG. 11, the microscope ocular portion 11a is clamped at four points inside a holding member 43e of C-shape in cross-section by means of resilient bodies 43a, 43b, 43c and 43d made of rubber or the like. The resilient bodies 43a and 43b are secured to the inner face of the holding member 43e by bonding or the like, while the resilient bodies 43c and 43d are secured by bonding or the like to one face of a single plate 43f inside the holding member 43e. A push rod 43g is secured to the other face of the plate 43f at right angles to this face, and is passed through a through hole formed in the holding member 43e. A spring 43h is passed over the push rod 43g so as to be positioned between the plate 43f and the holding member 43e. Accordingly, by pulling the push rod 43g so as to compress the spring 43h, the space between the resilient bodies 43a and 43b and the resilient bodies 43c and 43d is widened, after which the microscope ocular portion 11a is passed therethrough. Then by releasing the push rod 43g, the resilient bodies 43c and 43d are urged towards the microscope ocular portion 11a by the spring 43h. Therefore the microscope ocular portion 11a is clamped and secured between the resilient bodies 43a and 43b, and the resilient bodies 43c and 43d.

Figure 13:
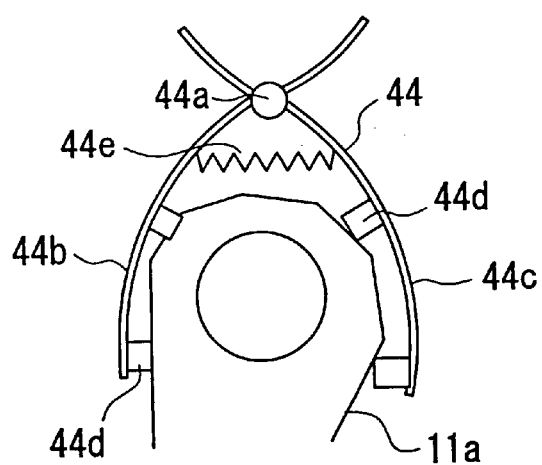
FIG. 13 is a plan view showing another modified example of a microscope gripping portion of the microscope gripping mechanism of FIG. 1.
Figure 14:
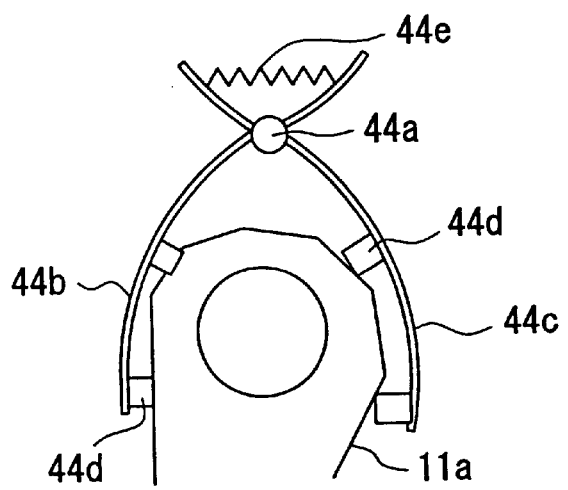
FIG. 14 is a plan view showing another modified example of a microscope gripping portion of the microscope gripping mechanism of FIG. 1.

Moreover, as shown in FIG. 13, there is also a securing method for effecting securing to the microscope ocular portion 11a, which uses a clip shape microscope gripping portion 44. That is to say, the microscope gripping portion 44 of FIG. 13 comprises; a pair of clamping members 44b and 44c rotatably secured at a fulcrum 44a, a plurality of resilient bodies 44d respectively secured to these so as to abut against the microscope ocular portion 11a, and a spring 44e secured between the respective clamping members 44b and 44c for bringing these towards each other. Consequently, by pressing the part of the clamping members 44b and 44c on the opposite side of the fulcrum 44a to that where the resilient bodies 44d are secured, the space between the clamping member 44b and the clamping members 44c is opened, and after inserting the microscope ocular portion 11a therein, the hand is removed so that this is clamped and secured by the force of the spring 44e. As a method of fitting the spring 44e, as shown in FIG. 14, this may involve fitting to the opposite side of the fulcrum 44a to that in FIG. 13. However, with the spring 44e in this case, the clamping force is produced by pushing wider the space between the clamping members 44b and 44c, of the part to which the spring 44e is attached.

Figure 15:
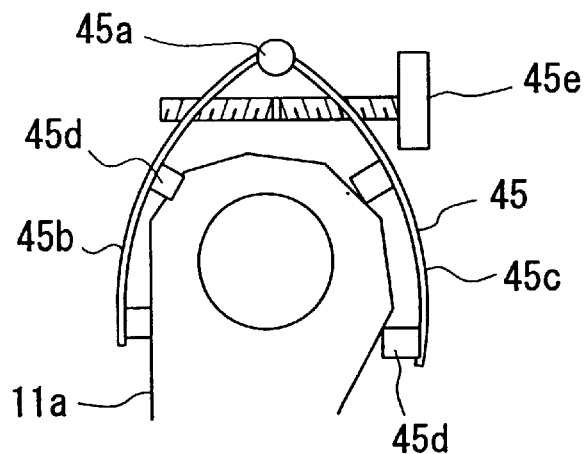
FIG. 15 is a plan view showing another modified example of a microscope gripping portion of the microscope gripping mechanism of FIG. 1.

Moreover, as shown in FIG. 15, there is also a securing method for securing by clamping with a compass-shaped microscope gripping portion 45. That is to say, the microscope gripping portion 45 comprises; a pair of clamping members 45b and 45c rotatably secured at a fulcrum 45a, a plurality of resilient bodies 45d respectively secured to these so as to abut against the microscope ocular portion 11a, and a male screw 45e threaded into respective female screw holes respectively formed in the clamping members 45b and 45c for widening and narrowing the space between the clamping member 45b and the clamping member 45c. By turning the male screw 45e in one direction the space is widened, and the microscope ocular portion 11a is passed therethrough. Then in this condition by turning the male screw 45e in the opposite direction, the space is narrowed thus effecting the claiming and securing method. With the male screw 45e, the winding direction of the thread is reversed at the approximate center in the axial direction thereof. Accordingly, the winding directions of the female threads of the clamping members 45b and 45c are opposite to each other. By means of this thread form, the distance between the clamping members 45b and 45c can be widened and narrowed by turning the male screw 45e.

The above described securing method of FIG. 7 through FIG. 15 has been described as a method for securing the microscope gripping mechanism 10 to the microscope ocular portion 11a. However a similar securing method can also be adopted for securing the endoscope ocular portion 13a to the microscope gripping mechanism 10.

Figure 16:
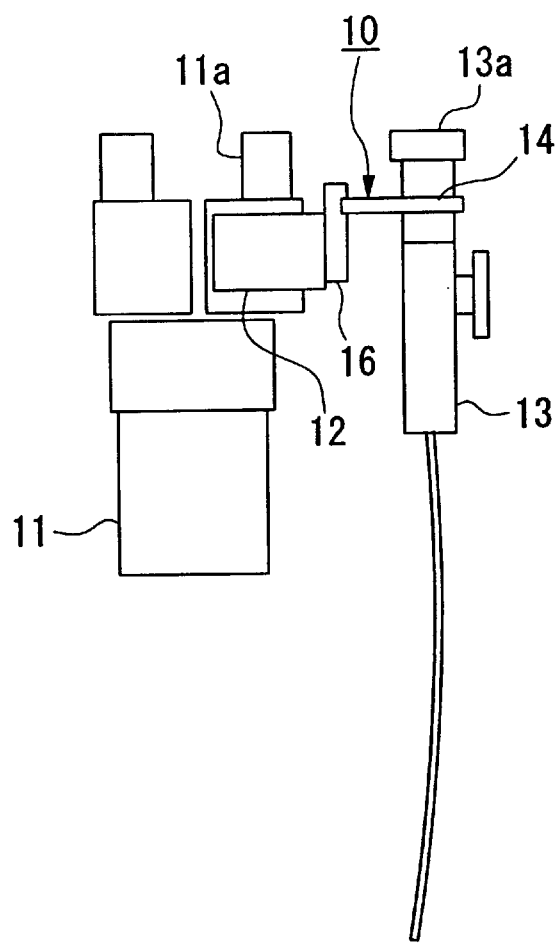
FIG. 16 is an elevation view showing a condition where the endoscope body of one configuration of the endoscope ocular portion is held by the microscope gripping mechanism of FIG. 1.

Furthermore, as a holding method for the endoscope 13 by means of the microscope gripping mechanism 10 (endoscope holder 10), the endoscope ocular portion 13a is held by the endoscope securing portion 14 as described above. However as shown for example in FIG. 16, this may involve holding the main body of the endoscope 13 of an integrated type endoscope ocular portion. In this case, instead of the above described securing method of FIG. 7 through FIG. 15, the holding method shown for example in FIG. 17 and FIG. 18 may be adopted.

Figure 17:
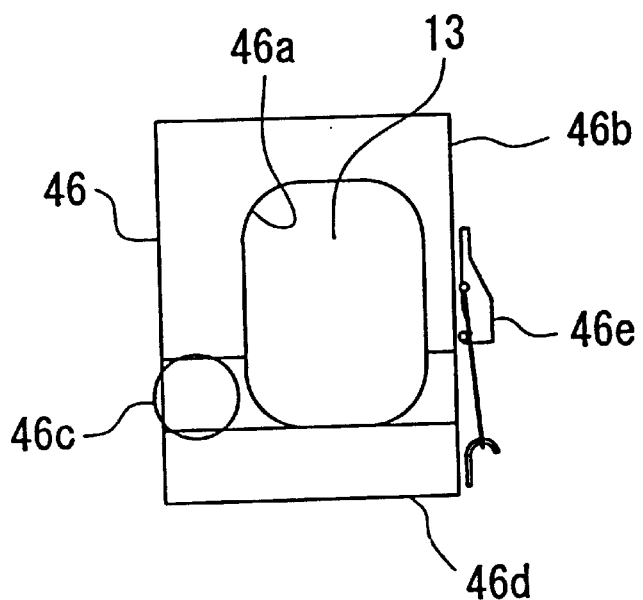
FIG. 17 is a plan view showing an example of an endoscope holding method for the microscope gripping mechanism of FIG. 1.

That is to say, a holding method shown in FIG. 17 is a clamping method where an endoscope securing portion 46 comprising; a clamping member 46b in which is formed a groove 46a for insertion of the endoscope 13 body, a clamping member 46d fixed to the clamping member 46b so as to be rotatable about a pin 46c, and a lock mechanism 46e for preventing opening of the space between the clamping members 46b and 46d, is used instead of the endoscope securing portion 14, to clamp the endoscope 13 body inside the groove 46a.

Figure 18:
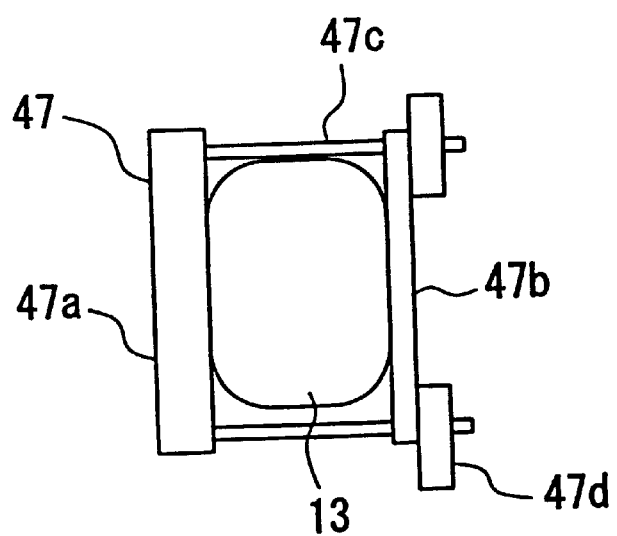
FIG. 18 is a plan view showing a modified example of the endoscope holding method.

A holding method shown in FIG. 18 is a holding method which uses an endoscope securing portion 47 with the endoscope 13 body inserted between a clamping member 47a and a clamping member 47b, and both secured by a plurality of threaded rods 47c and nuts 47d.

As shown in FIG. 19, the rotation direction of the endoscope image A of the endoscope 13 can be made the same (parallel) as the direction of the microscope image B of the medical microscope 11 by adjusting the rotation direction of the endoscope ocular portion 13a. As a result, agreement of the directions of the two images A and B is achieved, and hence the position and direction of the endoscope 13 can be easily ascertained.

Figure 20:
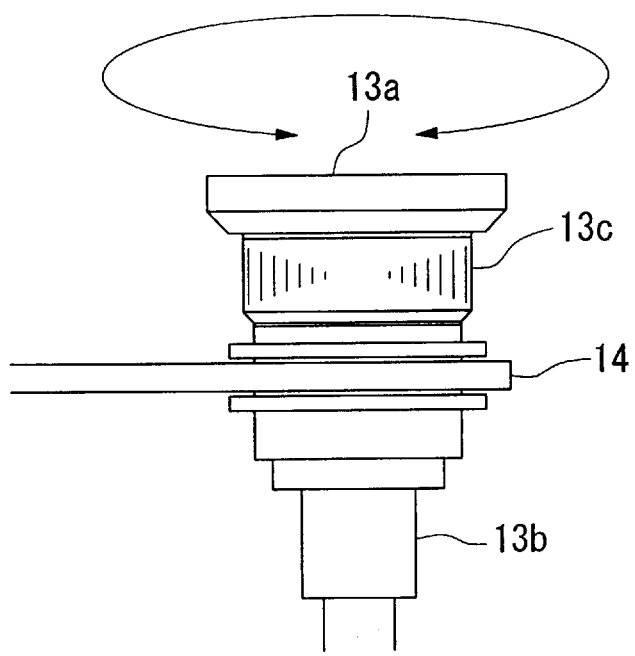
FIG. 20 is an explanatory diagram for explaining an adjustment method for the endoscope image direction of the endoscope which is held using the microscope gripping mechanism.
Figure 21:
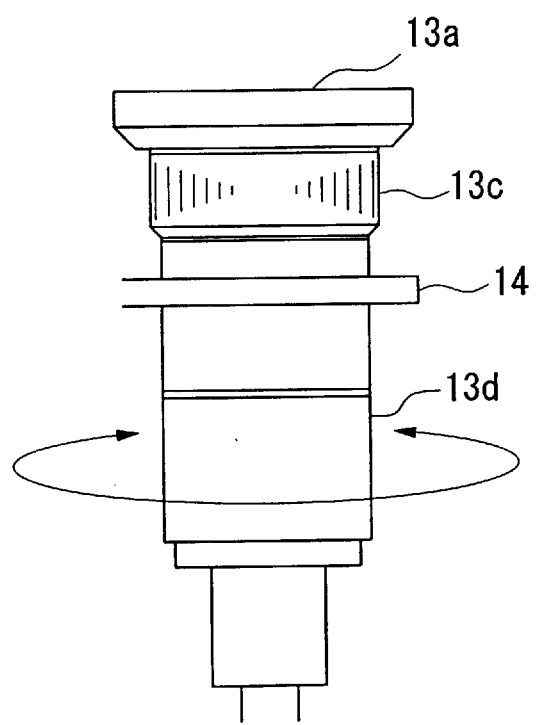
FIG. 21 is an explanatory diagram for explaining an other adjustment method for the endoscope image direction of the endoscope which is held using the microscope gripping mechanism.

In order to make this type of adjustment possible, it is considered to adopt, as shown in FIG. 20, an endoscope ocular portion 13a of a mechanism for rotating an eyepiece securing portion 13c rotatably fitted to a connector 13b, or to adopt, as shown in FIG. 21, an endoscope ocular portion 13a of a mechanism for rotating an eyepiece body tube portion 13d rotatably fitted to an eyepiece securing portion 13c.

Figure 22:
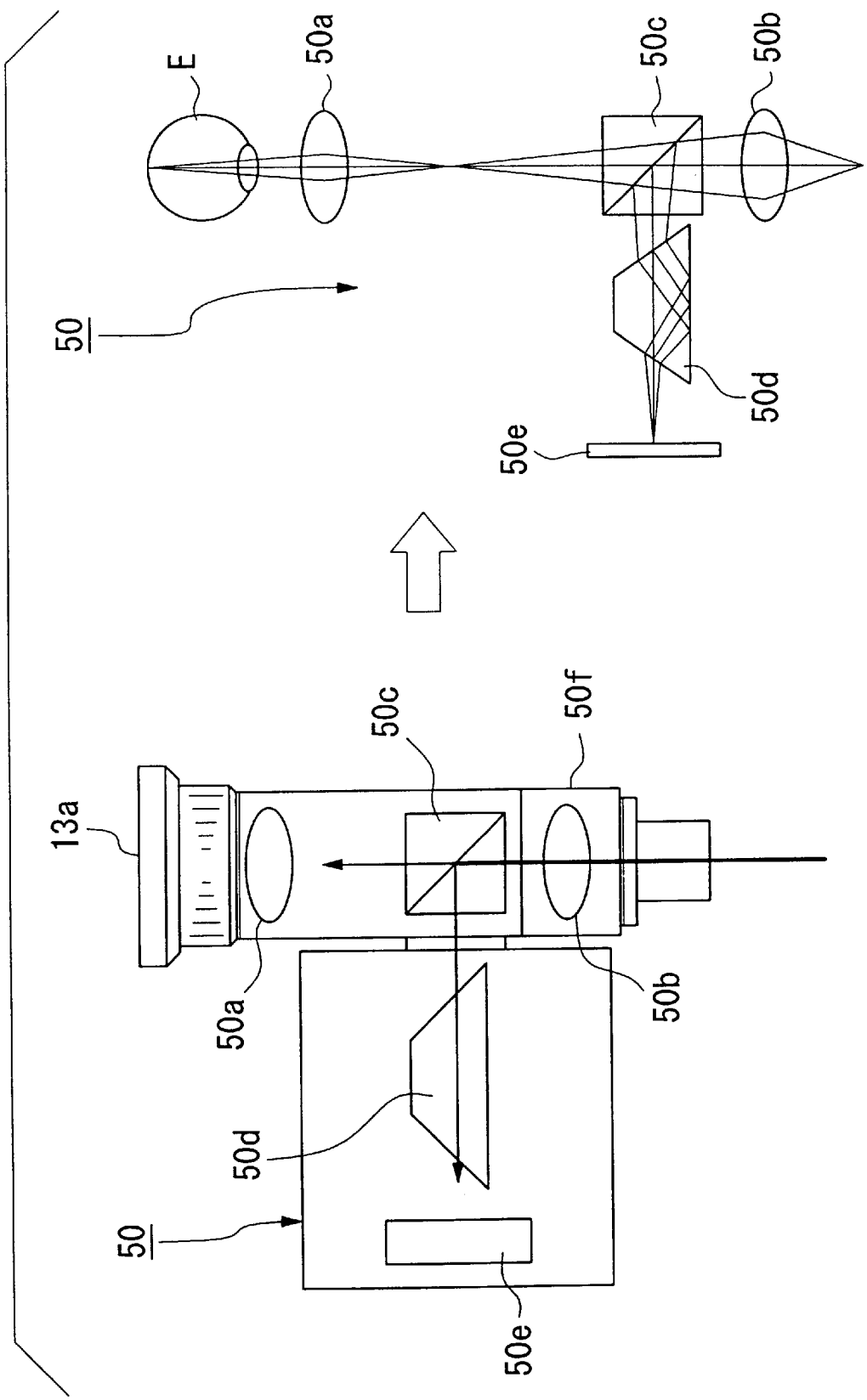
FIG. 22 is an outline explanatory diagram showing an example of where an imaging portion is provided on the endoscope.
Figure 23:
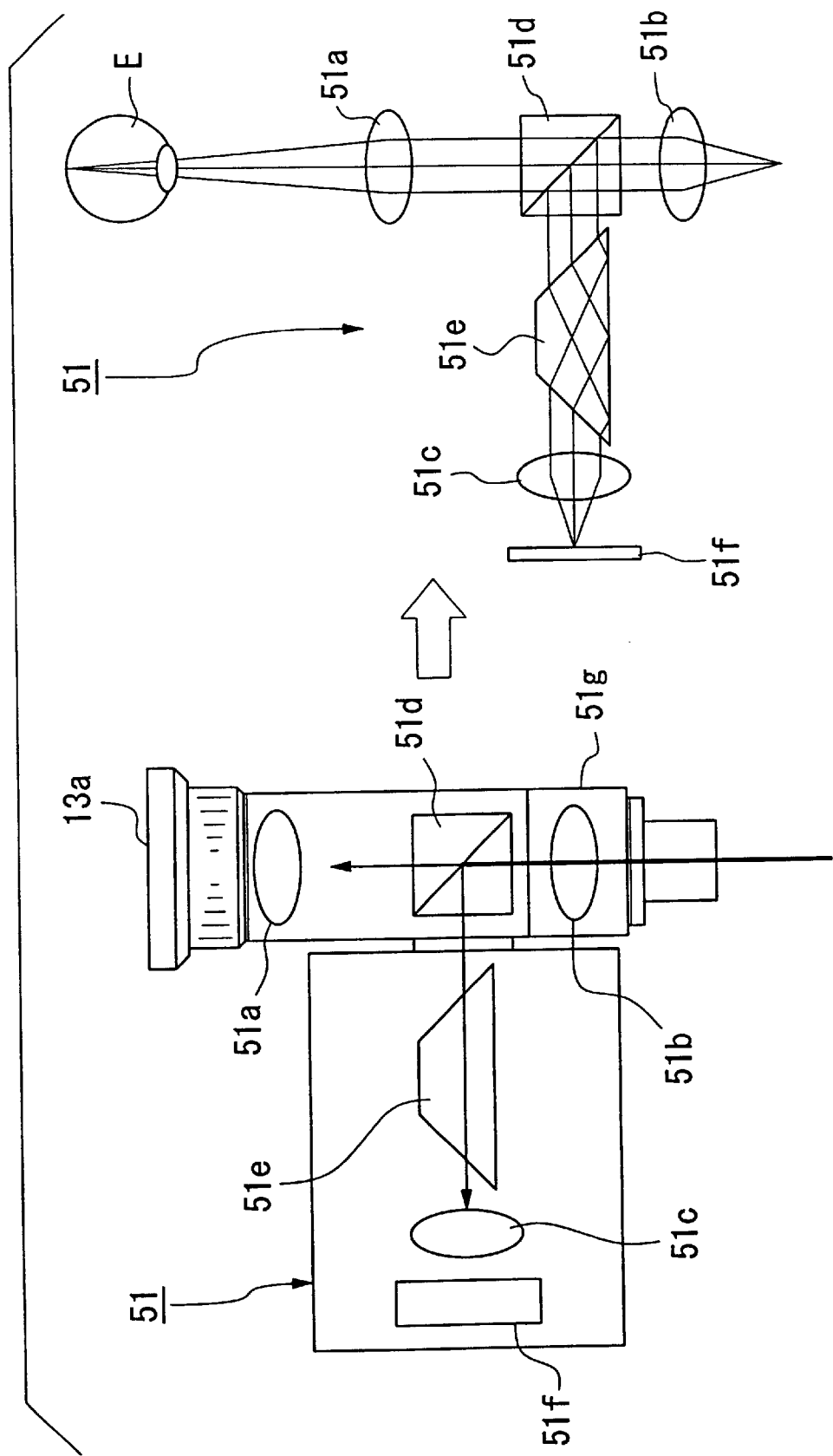
FIG. 23 is an outline explanatory diagram showing an example of where an other imaging portion is provided on the endoscope.

Moreover, as shown in FIG. 22 through FIG. 24, a construction may be adopted where an image receiving mechanism 50, 51, 52, being an optical-electrical device which can separately display and record the endoscope image, is provided at the endoscope ocular portion 13a of the endoscope 13, and this images on an imaging device such as a CCD camera or still camera or the like, and the observation image is recorded and displayed on a recording display device (not shown in the figure) so that this can be observed by a large number of people.

Reference symbols 50a and 50b shown in the left figure of FIG. 22 denote a lens system, reference symbol 50c denotes a half mirror or a beam splitter positioned between these, reference symbol 50d denotes an optical system such as a roof prism for left-right inversion of the endoscope image, while reference symbol 50e denotes an imager. The lens system 50b is secured inside a rotating part 50f, and can rotate together with the rotation of the rotating part 50f, about the axis of the endoscope ocular portion 13a. With the optical path in such a construction, as shown in the right figure of FIG. 22, an image the same as the endoscope image which reaches the eye E of the observer, is branched to the imager 50e and imaged and recorded.

Furthermore, reference symbols 51a, 51b and 51c shown in the left figure of FIG. 23 denote a lens system, reference symbol 51d denotes a half mirror or a beam splitter, reference symbol 51e denotes an optical system such as a roof prism for left-right inversion of the endoscope image, while reference symbol 51f denotes an imager. The lens system 51b is secured inside a rotating part 51g, and can rotate together with the rotation of the rotating part 51g, about the axis of the endoscope ocular portion 13a. With the optical path in such a construction also, similarly to FIG. 22, as shown in the right figure of FIG. 23, an image the same as the endoscope image which reaches the eye E of the observer, is branched to the imager 52f and imaged and recorded.

Figure 24B:
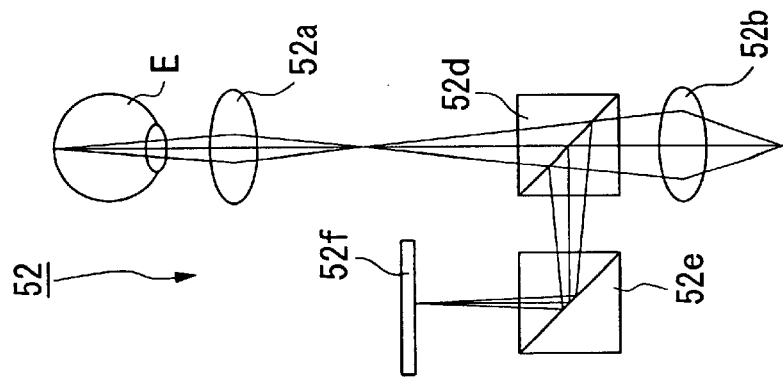
FIG. 24 is an outline explanatory diagram showing an example of where an other imaging portion is provided on the endoscope.
Figure 24A:
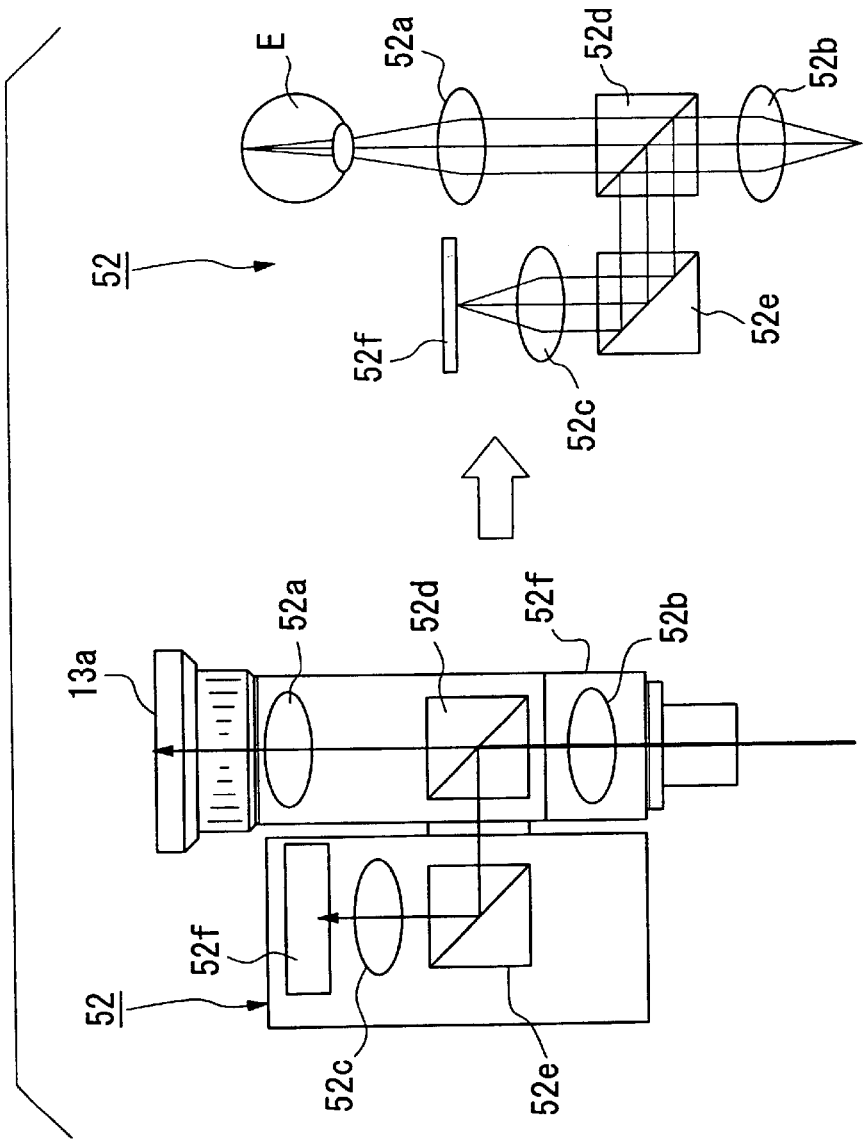

Moreover, reference symbols 52a, 52b and 52c shown in the left figure of FIG. 24A denote a lens system, reference symbol 52d denotes a half mirror or a beam splitter, reference symbol 52e denotes a 100% reflecting mirror, while reference symbol 52f denotes an imager. The lens system 52b is secured inside a rotating part 52g, and can rotate together with the rotation of the rotating part 52g, about the axis of the endoscope ocular portion 13a. With the optical path in such a construction also, similarly to FIG. 22, as shown in the right figure of FIG. 24A, an image the same as the endoscope image which reaches the eye E of the observer, is branched to the imager 52f and imaged and recorded. In the case where it is possible to directly image onto the imager 52f with the lens path of the lens 52b, the lens 52c becomes unnecessary, and this may be omitted as shown in FIG. 24B.

Figure 25:
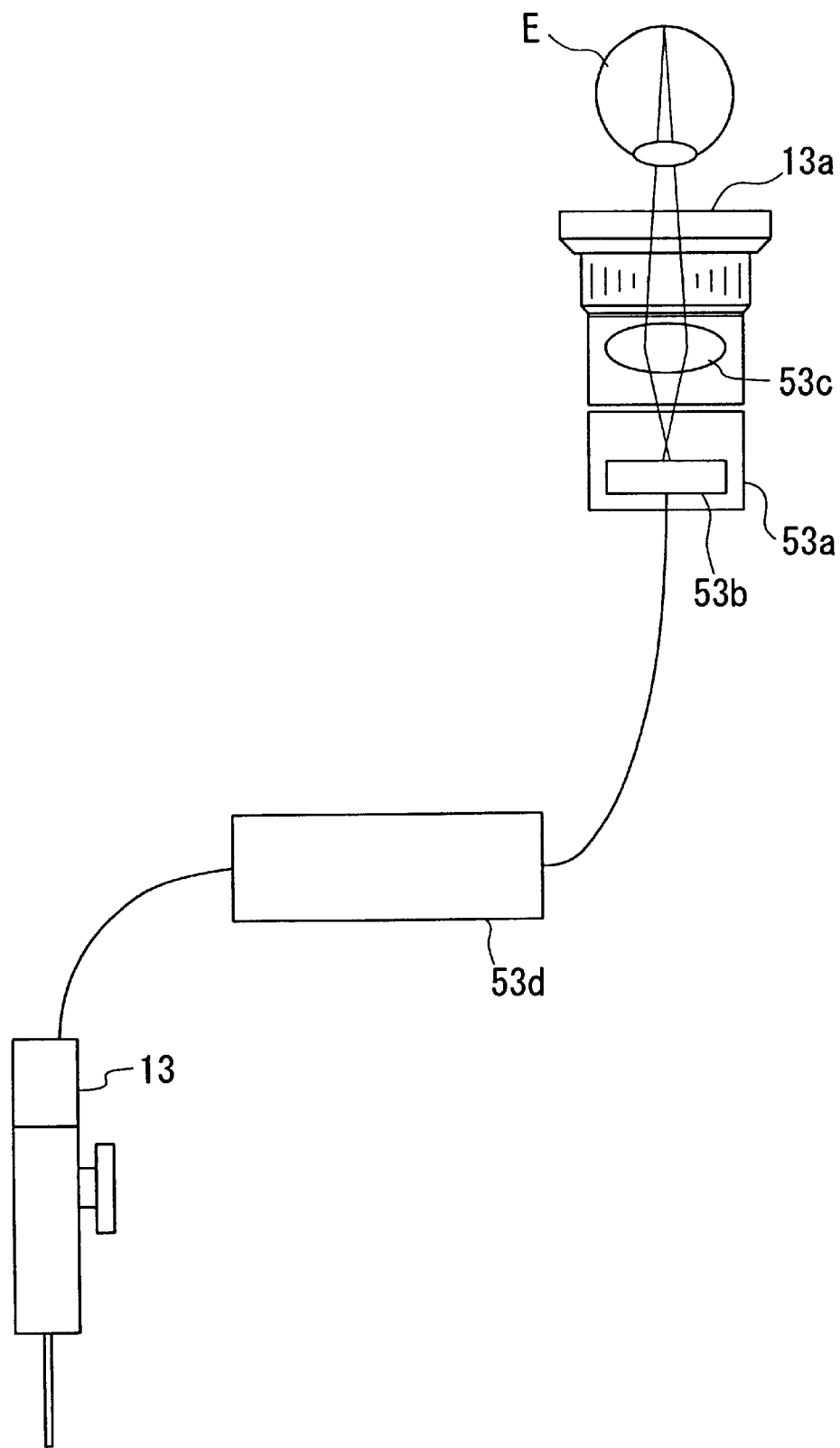
FIG. 25 is an outline explanatory diagram showing an example of an imaging portion incorporated into a video endoscope.

In the case where the endoscope 13 is a video endoscope, then by adopting a construction where a small size monitor portion 53b such as a liquid crystal or a small size CRT is housed inside a rotation portion 53a of the endoscope ocular portion 13a shown in FIG. 25, it is possible to obtain a similar effect to the above mentioned configurations of FIG. 22 through FIG. 24. Reference symbol 53c in FIG. 25 denotes a lens system, while reference symbol 53d denotes a controller for the endoscope 13.

Figure 26:
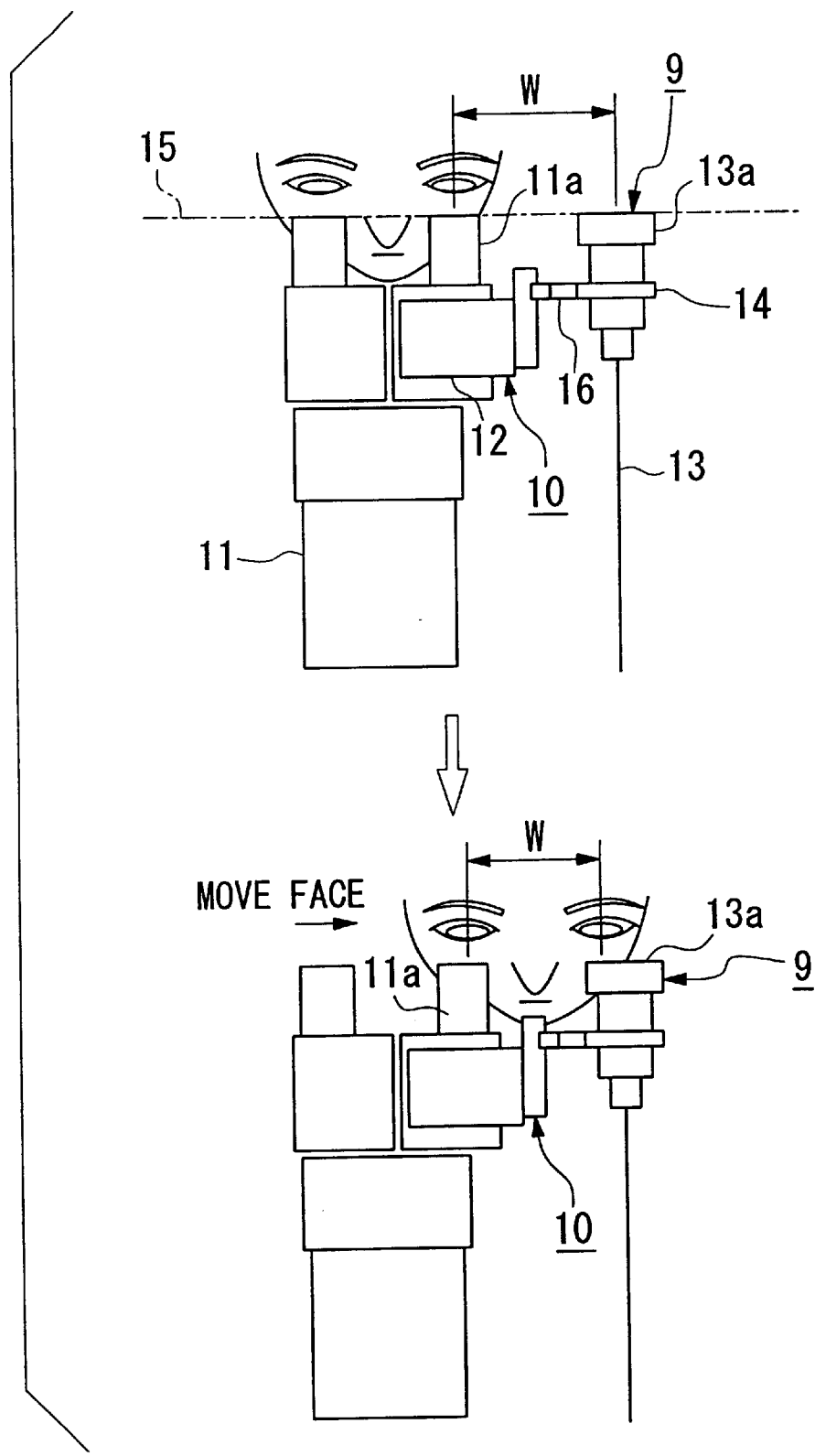
FIG. 26 is an explanatory diagram showing an observation method with the endoscope ocular portion secured to the microscope ocular portion using the microscope gripping mechanism of the present invention.
Figure 27:
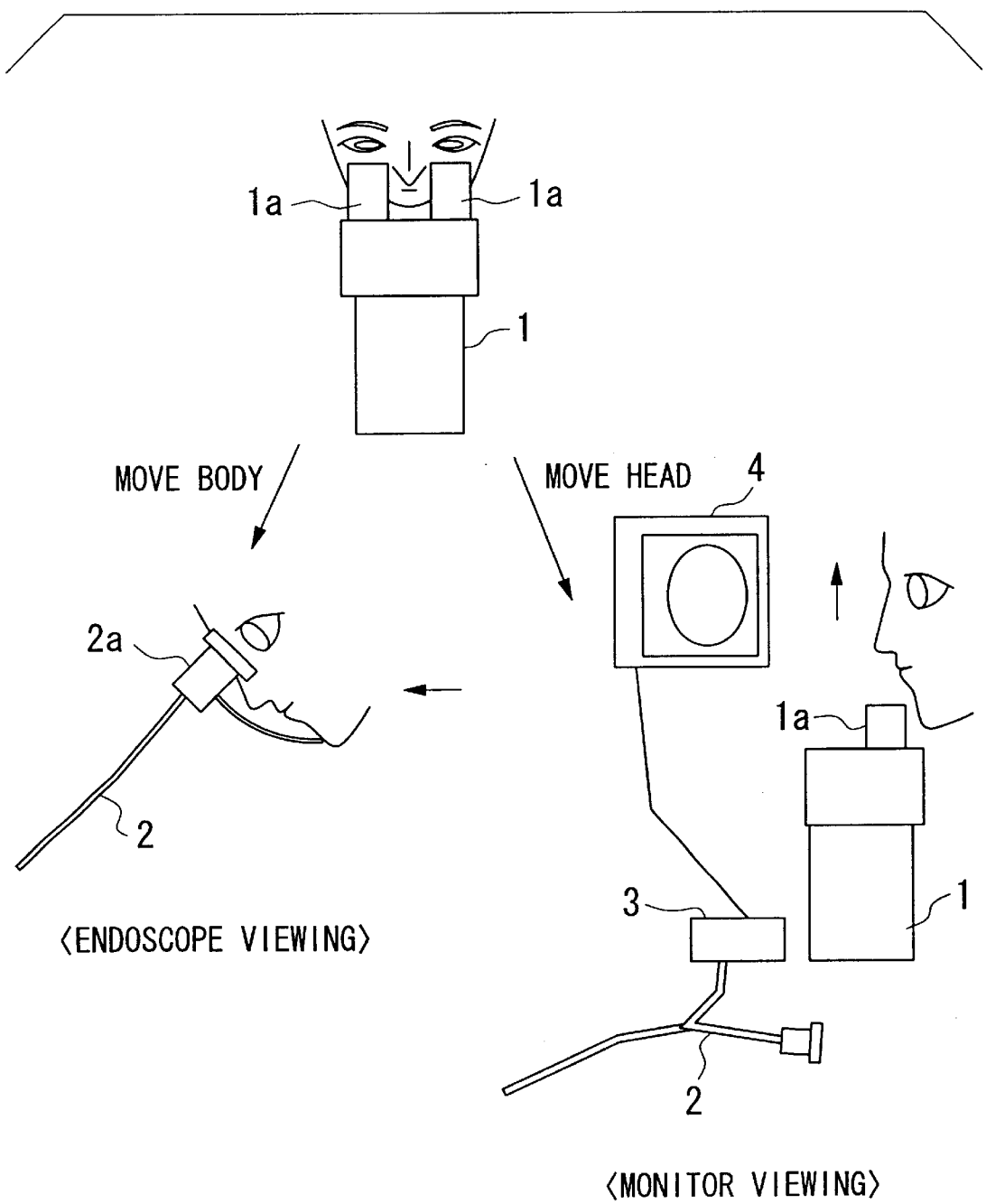
FIG. 27 is an explanatory diagram for explaining a conventional observation method using a medical microscope and an endoscope.

The endoscope securing method and viewing method using the microscope gripping mechanism 10 of the above described embodiments will be described hereunder with reference to FIG. 26. This endoscope securing method is one where the endoscope 13 such as a fiberscope or the endoscope ocular portion 13a, are fixed to the medical microscope 11. The endoscope securing portion 14 fixed to the endoscope 13 or the endoscope ocular portion 13a are secured via the linkage portion 16 to the microscope gripping portion 12 for gripping the medical microscope 11, and the endoscope ocular portion 13a and the microscope ocular portion 11a are positioned and secured on the same virtual plane 15, thus effecting the endoscope securing method. According to this endoscope securing method, the endoscope ocular portion 13a and the microscope ocular portion 11a are positioned and secured on the same virtual plane 15 and at approximately the same spacing W as the pupil distance of the observer. Hence the observer can look at the microscope ocular portion with one eye, and at the same time can look at the endoscope ocular portion with the other eye, and can thus view both the microscope image and the endoscope image simultaneously.

With the microscope gripping mechanism 10 and the endoscope securing method of the above mentioned embodiments, by using the low cost microscope gripping mechanism 10 with the construction having the microscope gripping portion 12 for gripping the medical microscope 11, the endoscope securing portion 14 secured to the endoscope 13, and the linkage portion 16 connected to these for positioning and securing the endoscope ocular portion 13a and the microscope ocular portion 11a on the same virtual plane 15 and at approximately the same spacing W as the pupil distance of the observer, it is possible to realize at low cost, simultaneous viewing of the medical microscope 11 and the endoscope 13 without the observer significantly moving their face or head.

Moreover, according to the microscope gripping mechanism 10 of the above mentioned embodiments, by having a construction where the endoscope securing portion 14 is relatively positioned in the horizontal direction and vertical direction with respect to the microscope gripping portion 12, and the inclination is adjusted with respect to the axis of the microscope gripping portion 12, the endoscope ocular portion 13a can be positioned and secured at an optimum position for easy observation corresponding for example to the orientation and position of the body and head of the observer.

What is claimed is:

1. An endoscope ocular portion fitted with a microscope gripping mechanism (9) where a microscope gripping mechanism (10) for gripping a medical microscope (11) is provided on an endoscope ocular portion (13a), wherein said microscope gripping mechanism has; a microscope gripping portion (12) for gripping said medical microscope, an endoscope securing portion (14) secured to said endoscope ocular portion, and a linkage portion (16) linking the microscope gripping portion and endoscope securing portion, and positioning and securing said endoscope ocular portion and a microscope ocular portion (11a) of said medical microscope on the same virtual plane (15) and at approximately the same spacing (W) as the pupil distance of an observer.

2. An endoscope ocular portion fitted with a microscope gripping mechanism according to claim 1, wherein with said endoscope securing portion, the relative position in the horizontal direction, the vertical direction and the rotation direction is adjustable with respect to said microscope gripping portion, and the inclination is adjustable with respect to the axis of said microscope gripping portion.

3. An endoscope ocular portion fitted with a microscope gripping mechanism according to either one of claim 1 and claim 2, wherein there is provided an optical-electrical device whereby with said endoscope ocular portion, an endoscope image can be directly view with the naked eye, and at the same time said endoscope image can be separately displayed and recorded.

4. An endoscope ocular portion fitted with a microscope gripping mechanism according to any one of claim 1 through claim 3, wherein said linkage portion links so that a plurality of separate arms can be folded and unfolded therebetween, and one end separate arm is connected to said endoscope securing portion, and an other end separate arm is connected to said microscope gripping portion so as to be slidably moveable in the axial direction of said microscope ocular portion.

5. An endoscope holder (10) which secures and holds an endoscope (13) such as a fiberscope to a medical microscope, said endoscope holder comprising: a microscope securing portion (12) secured to said medical microscope, an endoscope holding portion (14) for holding said endoscope, and a linkage portion linking said microscope securing portion and endoscope holding portion, and positioning and securing an endoscope ocular portion of said endoscope and a microscope ocular portion of said medical microscope on the same virtual plane and at approximately the same spacing as the pupil distance of an observer.

6. An endoscope holder according to claim 5, wherein with said endoscope holding portion, the relative position in the horizontal direction, the vertical direction and the rotation direction is adjustable with respect to said microscope securing portion, and the inclination is adjustable with respect to the axis of said microscope securing portion.

7. An endoscope holder according to either one of claim 5 and claim 6, wherein said linkage portion links so that a plurality of separate arms can be folded and unfolded therebetween, and one end separate arm is connected to said endoscope holding portion, and an other end separate arm is connected to said microscope securing portion so as to be slidably moveable in the axial direction of said microscope ocular portion.

8. An endoscope securing method where an endoscope such as a fiberscope is secured to a medical microscope, said method involving securing via a linkage portion an endoscope holding portion which holds said endoscope to a microscope securing portion which is secured to said medical microscope, and positioning and securing an endoscope ocular portion of said endoscope and a microscope ocular portion of said medical microscope on the same virtual plane and at approximately the same spacing as the pupil distance of an observer.

9. An endoscope securing method according to claim 8, wherein said linkage portion links so that a plurality of separate arms can be folded and unfolded therebetween, and one end separate arm is connected to said endoscope holding portion, and an other end separate arms is connected to said microscope securing portion so as to be slidably moveable in the axial direction of said microscope ocular portion.

10. The endoscope ocular portion fitted with a microscope gripping mechanism of claim 4, wherein with said linkage portion said respective separate arms can be folded and unfolded within a vertical plane.

11. An endoscope holder (10) which secures and holds an endoscope ocular portion to a medical microscope, said endoscope holder comprising: a microscope securing portion (12) secured to said medical microscope, an endoscope holding portion (14) for holding said endoscope ocular portion, and a linkage portion linking said microscope securing portion and endoscope holding portion, and positioning and securing said endoscope ocular portion and a microscope ocular portion of said medical microscope on the same virtual plane and at approximately the same spacing as the pupil distance of an observer.

12. An endoscope securing method where an endoscope ocular portion is secured to a medical microscope, said method involving securing via a linkage portion an endoscope holding portion which holds said endoscope ocular portion to a microscope securing portion which is secured to said medical microscope, and positioning and securing said endoscope ocular portion and a microscope ocular portion of said medical microscope on the same virtual plane and at approximately the same spacing as the pupil distance of an observer.

13. The endoscope holder of claim 7, wherein with said linkage portion said respective separate arms can be folded and unfolded within a vertical plane.

14. The endoscope securing method of claim 9, wherein with said linkage portion said respective separate arms can be folded and unfolded within a vertical plane.

* * * * *